(12) United States Patent
Sabbatini

(10) Patent No.: US 11,155,838 B2
(45) Date of Patent: *Oct. 26, 2021

(54) PROCESS TO PRODUCE A FERMENTATION PRODUCT

(71) Applicant: Versalis S.p.A., San Donato Milanese (IT)

(72) Inventor: Fabio Sabbatini, Siena (IT)

(73) Assignee: Versalis S.p.A, San Donato Milanese (IT)

(*) Notice: Subject to any disclaimer, the term of this patent is extended or adjusted under 35 U.S.C. 154(b) by 14 days.

This patent is subject to a terminal disclaimer.

(21) Appl. No.: 16/077,602

(22) PCT Filed: Feb. 20, 2017

(86) PCT No.: PCT/EP2017/053734
§ 371 (c)(1),
(2) Date: Aug. 13, 2018

(87) PCT Pub. No.: WO2017/144388
PCT Pub. Date: Aug. 31, 2017

(65) Prior Publication Data
US 2019/0055585 A1 Feb. 21, 2019

(30) Foreign Application Priority Data
Feb. 22, 2016 (EP) ..................... 16425017

(51) Int. Cl.
*C12P 7/06* (2006.01)
*C12P 7/14* (2006.01)
*C12P 7/64* (2006.01)

(52) U.S. Cl.
CPC ..... *C12P 7/14* (2013.01); *C12P 7/06* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 8,450,094 B1 | 5/2013 | Narandranath et al. | |
| 2014/0065700 A1 | 3/2014 | Narendranath et al. | |
| 2015/0252319 A1* | 9/2015 | De Bruijn | C12N 1/22 435/161 |

FOREIGN PATENT DOCUMENTS

| | | |
|---|---|---|
| WO | 2009155633 A1 | 12/2009 |
| WO | 2014072232 A1 | 5/2014 |
| WO | 2016193576 A1 | 12/2016 |

OTHER PUBLICATIONS

Schumm: "Cumulative effects of propagation, fermentation media, and inoculum size on the fermentation and economic performance of glucose and xylose co-fermentation by *Saccharomyces cerevisiae* 424A(LNH-ST)", Purdue University, West Lafayette, Indiana, U.S.A. Thesis, 2009, pp. Cover, i-ix, 1-104, XP002758004, Retrieved from the Internet: URL:http://search.proquest.com/docview/304990054 See pp. 32-33 (section 1.3.2), pp. 41-42 (section 2.2.4) and pp. 52-56 (sections 3.1-3.2.1).

Demeke et al: "Development of a D-xylose fermenting and inhibitor tolerant industrial *Saccharomyces cerevisiae* strain with high performance in lignocellulose hydrolysates using metabolic and evolutionary engineering", Biotechnology for Biofuels, vol. 6, 2013, p. 1, XP055223225, See p. 11 (right column/propagation) and p. 18 (Methods/propagated).

Slininger et al: "Evolved strains of Scheffersomyces stipitis achieving high ethanol productivity on acid- and base-pretreated biomass hydrolyzate at high solids loading", Biotechnology for Biofuels, vol. 8, 2015, pp. 1-27, XP021215588, See pp. 1-2 (Abstract and Background).

Nielsen et al: "Short-term adaptation during propagation improves the performance of xylose-fermenting *Saccharomyces cerevisiae* in simultaneous saccharification and co-fermentation", Biotechnology for Biofuels, vol. 8, 2015, pp. 1-15, XP002754256, See p. 3 (Propagation).

Dos Santos et al: "Second-generation ethanol: The need is becoming a reality", Industrial Biotechnology, vol. 12, Feb. 16, 2016 (Feb. 16, 2016), pp. 40-57, XP002757510, See p. 48 (Yeast propagation) and p. 51 (right column/Improving xylose consumption); online publication.

(Continued)

*Primary Examiner* — Soren Harward
*Assistant Examiner* — Paul D Pyla
(74) *Attorney, Agent, or Firm* — Edwin A. Sisson, Attorney at Law, LLC; Jeffrey J. Banyas

(57) ABSTRACT

It is disclosed a process to produce a fermentation product from a ligno-cellulosic feedstock hydrolyzate slurry which comprises water, water soluble glucose and xylose and water insoluble pretreated ligno-cellulosic feedstock. The process comprises at least two conversion step. A first conversion medium comprising a first portion of the ligno-cellulosic feedstock hydrolyzate slurry and a yeast capable to ferment glucose and xylose is first created, then the yeast is allowed to convert at least 50% of the glucose and less than 20% of the xylose of the first conversion medium to a first propagated yeast and a first portion of the fermentation product in a first conversion step having a first sugar-to-cells conversion ratio in a range of from 5% to 25%. A second conversion medium comprising at least a portion of the first propagated yeast and a second portion of the ligno-cellulosic feedstock hydrolyzate slurry is then created, then the yeast is allowed to convert at least a portion of the water soluble glucose and xylose in the second conversion medium to at least a second propagated yeast and a second portion of the fermentation product in a second conversion step having a second sugar-to-cells conversion ratio which is less than the first sugar-to-cells conversion ratio. Preferably, the first conversion step comprises at least a first phase which is an aerobic phase and a second phase which is an anaerobic phase.

17 Claims, 2 Drawing Sheets

(56) References Cited

OTHER PUBLICATIONS

Tomas-Pejo et al: "Influence of the propagation strategy for obtaining robust *Saccharomyces cerevisiae* cells that efficiently co-ferment xylose and glucose in lignocellulosic hydrolysates", Microbial Biotechnology, vol. 8, 2015, pp. 999-1005, XP002757398, See pp. 1000-1001 (Propagation strategy) and p. 1002 (Figure 2).

Bavouzet: De-risking fermentation, Biofuels International, 2015, pp. 70-71, XP002757522, Retrieved from the Internet: URL:http://www.lesaffreadvancedfermentatio ns.com/wp-content/uploads/2015/03/70-71_biofuelsmarch-april2015.pdf [retrieved on May 10, 2016] See p. 70 (Ceilux) and p. 71 (Figures).

Guo et al: Construction of yeast strain capable of co-fermenting pentose and hexose by protoplast fusion, Advanced Materials Research, vol. 781-784, 2013, pp. 847-851, XP002757399, See p. 847 (Abstract and Introduction).

Lorliam et al: "First determination of ethanol production and xylose reductase gene of *Zygoascus meyerae* E23", Chiang Mai Journal of Science, vol. 41, 2014, pp. 231-236, XP002757525, See pp. 231-232 (Introduction).

\* cited by examiner

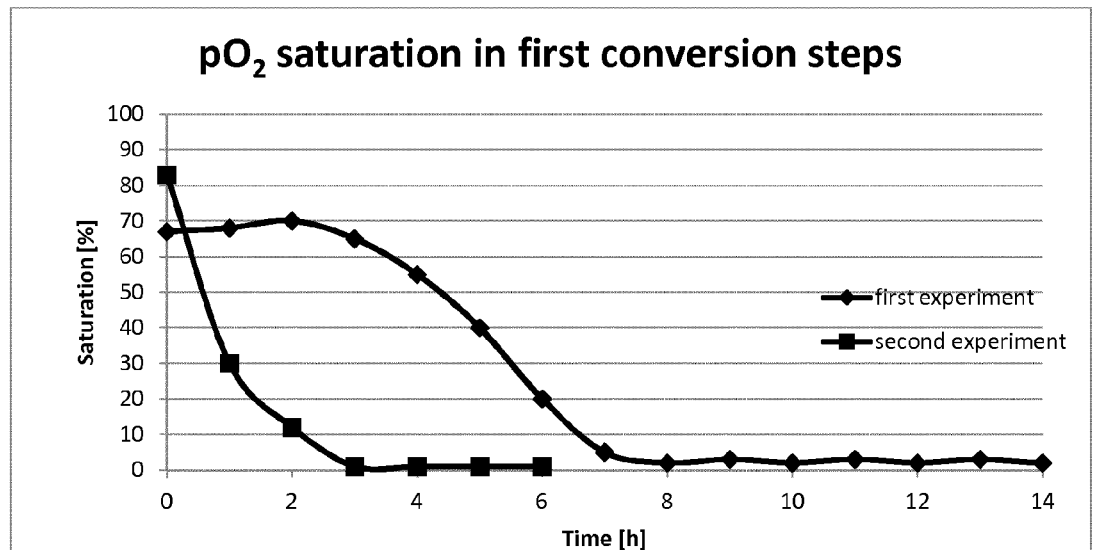
FIGURE 1. Oxygen saturation in the first conversion steps

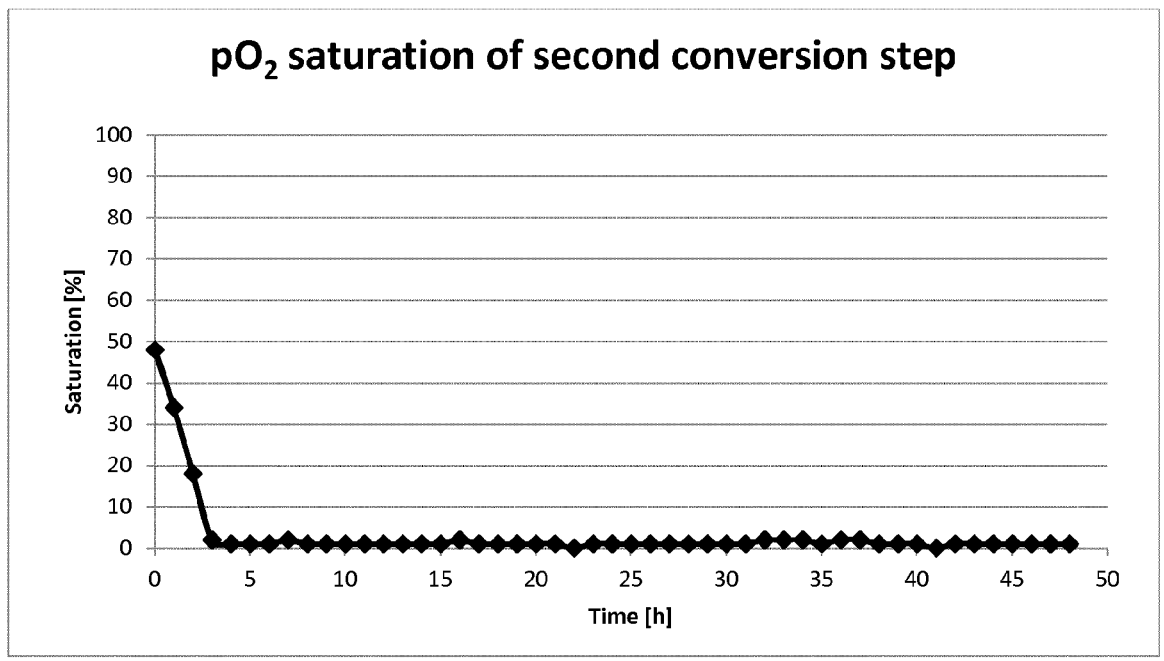
FIGURE 2. Oxygen saturation in the second conversion step of first lab scale experiment

PROCESS TO PRODUCE A FERMENTATION PRODUCT

PRIORITIES AND CROSS REFERENCES

This application claims priority from International Application No. PCT/EP2017/053734 filed on 20 Feb. 2017 which claims priority from European Application No. 16425017.7 filed on 22 Feb. 2016, the teachings of each of which are incorporated by reference herein in their entirety.

BACKGROUND

The fermentation of monomeric sugars to alcohol by means of yeast is very well known since thousands of years. Namely, beer has been produced by almost all the cultures and populations in the history of human kind. In the field of biofuels, first generation feedstocks having a high starch content, such as corn, have been successfully used on industrial scale to produce ethanol. Fermentative processes of first generation technology take advantage from the facility to hydrolyze the feedstock to produce an hydrolyzed mash having a very high concentration of monomeric C6 sugars, prevalently glucose, and very few or no yeast inhibitors, such as acetic acid. Moreover, no hemicellulose derived sugars such as xylose are present in first generation feedstock.

The use of a ligno-cellulosic feedstock hydrolyzate presents a series of demanding problems, most of them arising in conducting the process on industrial scale. Most of the problems are related to render the process economically feasible, others are connected to specific characteristics of the ligno-cellulosic feedstock hydrolyzate which render the use of a ligno-cellulosic feedstock hydrolyzate more difficult than in the case of a first generation hydrolyzate.

A first drawback in fermenting a ligno-cellulosic feedstock hydrolyzate is the presence of C5 monomeric sugars, mainly xylose. Xylose is known to be difficult or impossible to be converted by natural enzymes and yeasts, and special genetically modified enzyme cocktails and yeasts have been engineered to convert the hemicellulosic portion. Even with yeast genetically modified to be capable of fermenting both glucose and xylose, xylose conversion is slow.

A second drawback in fermenting a ligno-cellulosic feedstock hydrolyzate is the low sugar concentration of a ligno-cellulosic feedstock hydrolyzate, which is typically less than 100 gr of total sugars per kg of hydrolyzate on a wet basis. At low sugar concentration, sugar uptake rate by the yeast is slow and thereby it is facilitated the propagation of biological contaminants, such as bacteria, which consume a relevant portion of the available sugars to produce unwanted bio-products, such as lactic acid. The problem is further enhanced by the slow xylose conversion rate by the yeast. Thereby, sterilization of the ligno-cellulosic feedstock hydrolyzate by means of chemical or bio-chemical agents, such as antibiotics, or by means of physical agents, such as heat or light, is often practiced, increasing the whole costs.

A third drawback in fermenting a ligno-cellulosic feedstock hydrolyzate is the presence of inhibitory compounds in the hydrolyzate. Compounds such as acetic acid, formic acid, furfural, which are typically produced in pre-treating or hydrolyzing the ligno-cellulosic feedstock, reduce the yeast capability to uptake sugars, or at least the uptake rate. Removal of inhibitory compounds at various stages upstream to the yeast conversion is often practiced, again increasing the whole costs.

One main problem in a fermentation process of a ligno-cellulosic feedstock hydrolyzate is to reduce the amount of yeast totally needed, which has a great impact on end product cost. To solve the problem, a propagation step is usually practiced, wherein yeast is inserted in a propagation medium under conditions promoting the yeast growth, thereby allowing to produce more yeast cells to be used in a following fermentation process. Propagation may be conducted in batch, fed-batch and continuous mode. While propagation of a yeast on a propagation medium comprising synthetic sugars—both xylose and glucose—has been demonstrated to be effective on a lab scale, different approaches have been proposed to propagate the yeast on a ligno-cellulosic feedstock hydrolyzate to reduce costs of propagation medium.

Typically, the whole process for converting a ligno-cellulosic feedstock hydrolyzate to a fermentation products is separated in one or more propagation steps, followed by one or more fermentation steps. The propagation and fermentation steps are specialized to produce a specific product. The propagation step is conducted to devote the maximum allowed amount of the carbon in the propagation medium to produce yeast cells, minimizing the amount of carbon converted to other products, such as ethanol, which are considered by-products in the propagation step. The fermentation step is instead conducted to maximize the amount of the carbon in the fermentation medium to produce ethanol, which is the final fermentation product, by means of the yeast propagated in the propagation step. The propagation step is conducted in aerobic conditions, thereby air at a high flow must be inserted in the ligno-cellulosic feedstock hydrolyzate and the ligno-cellulosic feedstock hydrolyzate must be agitated at high intensity for promoting the contact of the yeast with air. The ligno-cellulosic feedstock hydrolyzate is often produced in a slurry form, thereby it is difficult and expensive to be agitated. The ligno-cellulosic feedstock hydrolyzate slurry may be separated in a liquid component comprising water and water soluble glucose and xylose, and a solid component comprising water insoluble pretreated ligno-cellulosic feedstock, again increasing the process costs.

WO2009155633A1 discloses the use of a substrate comprising C5 compound-containing material, in the growth of *Saccharomyces* yeast or the production of a product of *Saccharomyces* yeast, wherein the C5 compound-containing material is: (a) C5 compound-containing material obtained from ligno-cellulosic hydrolysate; (b) C5 compound-containing material obtained from fermentation of ligno-cellulosic hydrolysate; or (c) a mixture of (a) and (b). The patent application also discloses a method of producing *Saccharomyces* yeast biomass or a product of *Saccharomyces* yeast using the substrate, the method comprising incubating a substrate comprising a C5 compound-containing material with a *Saccharomyces* yeast in conditions which cause growth of the *Saccharomyces* yeast or production of the product. Therefore, the patent application is silent about specific problems and related solutions involved in yeast propagation on a ligno-cellulosic hydrolysate.

WO2014072232A1 discloses a process for the aerobic propagation of yeast wherein the yeast is grown in a reactor, comprising the steps of: a) filling the reactor with a carbon source and an initial yeast population, b) optionally growing the initial yeast population in the reactor in batch mode, c) measuring the pH in the reactor, d) adding ligno-cellulosic hydrolysate to the reactor in fed batch mode at a rate to set the pH in the reactor at a predetermined value, and e) after sufficient propagation, isolation of yeast from the reactor.

The carbon source of step a) may be diluted ligno-cellulosic hydrolysate, wherein dilution of the ligno-cellulosic hydrolysate is provided for reducing the effects of inhibitor compounds of the ligno-cellulosic hydrolysate. Controlling a growth in fed batch mode is difficult on an industrial scale, and increases costs, as well as maintaining aerobic conditions in a propagation process on a ligno-cellulosic hydrolysate, which requires strong agitation and high air flow. Moreover, the patent application does not recognize the presence of biological contaminants as critical in the propagation step. Namely, it is stated that bacterial or wild yeast contamination is rarely a problem during propagation because yeast propagation tanks are smaller and can be more easily cleaned than fermentation tanks. Apart from cleaning, antibacterial products may be added to prevent growth of unwanted microbes.

U.S. Pat. No. 8,450,094 discloses a method of propagating a yeast on a medium for propagation, wherein xylose is supplied to the medium as a carbon source for cell mass growth. A first cell mass is propagated under aerobic conditions with an airflow of at least 1.0 volumes of air per volume of medium per minute in a second cell mass, which is optionally propagated in a following step in a third cell mass. The sequential method disclosed in the patent to produce a reasonable amount of yeast requires long propagation times in condition favorable to biological contaminants, thereby requiring the sterilization of the carbon source.

There is thereby the need of an industrial process to produce a fermentation product from a ligno-cellulosic feedstock hydrolyzate in a slurry form, wherein at the same time it is produced the majority of the yeast needed. It is believed that the disclosed process overcomes the above mentioned drawbacks in using a ligno-cellulosic feedstock hydrolyzate slurry, providing a cost effective solution for producing a fermentation product from a ligno-cellulosic feedstock hydrolyzate on an industrial scale.

SUMMARY

This specification disclose a process to produce a fermentation product from a ligno-cellulosic feedstock hydrolyzate slurry comprising water, water soluble glucose and water soluble xylose and water insoluble pretreated lignocellulosic feedstock, said process comprising the steps of: Creating a first conversion medium comprising a first portion of the ligno-cellulosic feedstock hydrolyzate slurry and a yeast capable of converting glucose and xylose to a propagating yeast and a fermentation product; allowing the yeast to convert at least 50% of the water soluble glucose and less than 20% of the water soluble xylose of the first conversion medium to a first propagated yeast and a first portion of the fermentation product in a first conversion step having a first sugar-to-cells conversion ratio in a range of from 5% to 25%, wherein the first sugar-to-cells conversion ratio is a percent weight ratio of the glucose and xylose converted to the propagated yeast in the first conversion step to the water soluble glucose and xylose totally converted in the first conversion medium, on a carbon basis; creating a second conversion medium comprising at least a portion of the first propagated yeast and a second portion of the ligno-cellulosic feedstock hydrolyzate slurry; allowing the yeast to convert at least a portion of the water soluble glucose and xylose in the second conversion medium to at least a second propagated yeast and a second portion of the fermentation product in a second conversion step having a second sugar-to-cells conversion ratio which is less than the first sugar-to-cells conversion ratio, wherein the second sugar-to-cells conversion ratio is a percent weight ratio of the water soluble glucose and xylose converted to the propagated yeast in the second conversion step to totally converted water soluble glucose and xylose in the second conversion medium, on a carbon basis.

It is also disclosed that the first conversion step may comprise at least a first phase which is an aerobic phase and a second phase which is an anaerobic phase, wherein the aerobic phase are conducted for a time in a range from 3 hours to 12 hours.

It is further disclosed that the first conversion step may be conducted for a first conversion time which is less than a value selected from the group consisting of 30 hours, 20 hours, 15 hours, and 10 hours.

It is also disclosed that the first conversion step may be conducted by inserting air at a flow rate which is in a range selected from the group consisting of from 0.1 vvh to 10 vvh, from 0.1 vvh to 5 vvh, and from 0.5 vvh to 3 vvh.

It is further disclosed that the first conversion step may be conducted by mixing the first conversion medium at a weight power density of less than 100 W/ton of the first conversion medium on a wet basis.

It is also disclosed that the first sugar-to-cells conversion ratio may be in a range selected from the group consisting of from 5% to 20%, and from 10% to 20%.

It is further disclosed that the second conversion step may be conducted in anaerobic conditions for at least 80% of the second conversion time.

It is also disclosed that the second conversion step may be conducted for a second conversion time which is greater than the first conversion time and less than a value selected from the group consisting of 72 hours, 60 hours, and 50 hours.

It is further disclosed that at least 80% of the water soluble glucose and water soluble xylose may be converted in the second conversion step.

It is also disclosed that the second sugar-to-cells conversion ratio may be greater than 2%.

It is further disclosed that the dry matter of the first and second conversion media may be less than 30% and greater than a percent value selected from the group consisting of 5%, 10%, 15%, and 20%.

It is also disclosed that the first conversion medium and the second conversion medium may further comprise a nitrogen source.

It is further disclosed that no vitamins and/or trace elements may be added to the process.

It is also disclosed that the ligno-cellulosic feedstock hydrolyzate slurry may not be subjected to any sterilization.

It is further disclosed that the first conversion step may have a starting yeast density between $1\times10^6$ and $1\times10^8$ yeast cells per milligram of the first conversion medium on a wet basis.

It is also disclosed that the first conversion step may have a final yeast density which is between $1\times10^7$ and $1\times10^9$ yeast cells per milligram of the first conversion medium on a wet basis.

It is further disclosed that the second conversion step may have a starting yeast density which is greater than the starting yeast density in the first conversion step.

It is also disclosed that the first conversion step and the second conversion step may be conducted in separated vessel.

It is further disclosed that the fermentation product may be ethanol.

BRIEF DESCRIPTION OF FIGURES

FIG. 1 is the Oxygen saturation curve in the first conversion step of two experimental test on lab scale FIG. 2 is the Oxygen saturation curve in the second conversion step of two experimental test on lab scale

DETAILED DESCRIPTION

This specification discloses a process comprising at least two sequential conversion steps of a ligno-cellulosic feedstock hydrolyzate slurry to a fermentation product by means of a yeast, wherein at the same time in each step a portion of the total amount of water soluble glucose and xylose of the ligno-cellulosic feedstock hydrolyzate is converted to yeast cells used in the disclosed process. The yeast cells produced in the first conversion step are called a first propagated yeast and are then used in the second conversion step. In each step, the fermentation product is thereby the main conversion product, but the first conversion step is conducted in conditions more favorable to yeast propagation than in the second conversion step. Thereby in the first conversion step the percent of the total amount of water soluble glucose and water soluble xylose converted to yeast is greater than the percent of the total amount of water soluble glucose and water soluble xylose converted to yeast in the second conversion step. In each conversion step, there is a sugar-to-cells conversion ratio. The sugar-to-cells conversion ratio is the percent weight ratio of the amount of water soluble glucose and water soluble xylose converted to yeast to the amount of water soluble glucose and water soluble xylose which is totally converted in that step on a carbon basis and expressed as a percent, and not to the amount of water soluble glucose and xylose totally available in the step. For sake of clarity, the sugar-to-cells conversion ratio of the amount of water soluble glucose and xylose totally converted in the first conversion step may be less than in the second conversion step. This may occurs, for instance, in the case that the first conversion step is conducted for a first conversion time which is shorter than the conversion time of the second conversion step. But, relative to the respective converted fraction of water soluble glucose and xylose, yeast propagation in the first conversion step is more favorable than in the second conversion step. The water soluble glucose and xylose which are not converted in the first conversion step are not wasted, as they are preferably introduced and converted in the second conversion step.

According to one aspect, the disclosed process provides a solution which can be implemented on industrial scale, overcoming the problems occurring in a real conversion plant.

According to another aspect, the disclosed process permits to produce the yeast needed for producing the fermentation product starting from a small amount of yeast, thereby sensitively reducing the fermentation costs.

According to a further aspect, in the disclosed process the yeast propagation occurs on a ligno-cellulosic feedstock hydrolyzate slurry already available in the conversion plant, thereby avoiding or greatly reducing the costs associated with expensive carbon sources.

According to a further aspect, the disclosed process enables the use of a ligno-cellulosic feedstock hydrolyzate slurry which may contain biological contaminants at a non-negligible level, without the use of any sterilization agent or procedure.

According to a further aspect, the disclosed process may be conducted without the use of vitamins and other expensive nutrients.

In the context of the present disclosure, the expression "converting a water soluble sugar" is used to indicate a process to produce a general product from the water soluble sugar; the general product comprises a propagation product, which is a new yeast biomass, and a fermentation product, such as ethanol.

By "propagating a yeast", or "yeast growth", or "producing a yeast", "converting to a yeast", and "converting to a propagated yeast" it is meant the process of increasing the amount of yeast, or yeast biomass, obtained by feeding an initial yeast amount with a carbon source and optionally other nutrients in suitable conditions. The increase of the yeast biomass or yeast amount occurs by increasing the number of yeast cells totally produced, and it may be verified by determining the cells density at the beginning and at the end of the propagation step(s) or conversion step(s), or during the propagation or conversion step or steps. Cell density may be determined by counting the yeast cells present in representative samples of the conversion medium at different times of the propagation step or steps.

The yeast of the disclosed process is capable of fermenting not only C6 monomeric sugars, preferably glucose, but also C5 monomeric sugars, preferably xylose. As a naturally occurring yeast is typically not capable of up-taking xylose, the yeast used in the disclosed process is preferably a non-naturally occurring yeast or derived from a non-naturally occurring yeast.

The term "non-naturally occurring" yeast means that the microbial organism has at least one genetic alteration not normally found in a naturally occurring strain of the referenced species, including naturally occurring strains of the referenced species, in order to render the naturally occurring yeast capable to ferment both glucose and xylose. Genetic alterations may include, for example, modifications introducing expressible nucleic acids encoding metabolic polypeptides, other nucleic acid additions, nucleic acid deletions and/or other functional disruption of the yeast genetic material. Such modifications may include, for example, coding regions and functional fragments thereof, for heterologous, homologous or both heterologous and homologous polypeptides for the referenced species. Additional modifications may include, for example, non-coding regulatory regions in which the modifications alter expression of a gene or operon.

The non-naturally occurring yeast of the present disclosure can contain stable genetic alterations, which refers to yeast that can be propagated for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

The yeast of the present disclosure can be selected from any known genus and species of yeasts. Yeasts are described for example by N. J. W. Kreger-van Rij, "The Yeasts," Vol. 1 of Biology of Yeasts, Ch. 2, A. H. Rose and J. S. Harrison, Eds. Academic Press, London, 1987. In one embodiment the yeast is selected from the group consisting of *Saccharomyces, Zygosaccharomyces, Candida, Hansenula, Kluyveromyces, Debaromyces, Nadsonia, Lipomyces, Torulopsis, Kloeckera, Pichia, Schizosaccharomyces, Trigonopsis, Bret-*

*tanomyces, Cryptococcus, Trichosporon, Aureobasidium, Lipomyces, Phaffia, Rhodotorula, Yarrowia*, and *Schwanniomyces*. Preferably the yeast is selected from *Saccharomyces cerevisiae* strains.

In the disclosed process, the main carbon source used is a hydrolyzate in a slurry form derived from a ligno-cellulosic feedstock. A detailed description of a ligno-cellulosic feedstock may be found in WO2015028156A1, pag. 11-14, which is herein incorporated by reference. A preferred ligno-cellulosic feedstock is selected from the group of agricultural residues, in particular straws such as wheat straw, rice straw, or bagasse, such as sugar cane bagasse. The hardwoods and softwoods also benefit from this process. Optionally, other carbon sources such as molasse or synthetic sugars may also be used, but the monomeric sugars of the ligno-cellulosic feedstock hydrolyzate are preferably at least 80% by weight, more preferably at least 90%, and most preferably at least 95% of the total carbon sources used in the process. In an even most preferred embodiment, the ligno-cellulosic feedstock hydrolyzate is the unique carbon source used in the disclosed process for propagating the yeast.

The ligno-cellulosic feedstock hydrolyzate slurry is preferably derived from the ligno-cellulosic feedstock by means of a multi-step process comprising pre-treating the ligno-cellulosic feedstock to produce a pre-treated ligno-cellulosic feedstock and subjecting the pre-treated ligno-cellulosic feedstock to enzymatic hydrolysis. The pre-treatment increases the accessibility of the carbohydrates therein contained to the action of enzymes. A preferred pretreatment comprises hydrothermally treating the ligno-cellulosic feedstock with water in steam phase in a pressurized reactor, and steam exploding the hydrothermally treated feedstock by rapidly releasing the pressure applied to the feedstock. The hydrothermal treatment is conducted preferably at a temperature in a range from 130° C. to 230° C. for a time from 1 minute to 180 minutes. The reactor is preferably pressurized by steam at a pressure of at least 10 bar to obtain an effective breaking-up of the feedstock.

In one embodiment, the ligno-cellulosic feedstock is subjected to a soaking process or step to remove a portion of non-ligno-cellulosic compounds contained in the raw ligno-cellulosic feedstock such as inorganic salts, waxes, and organic acids prior to being hydrothermally treated in the pressurized reactor. In the soaking step or process, external contaminants, such as ground, stones, and harvesting residues may also be separated. The soaking process preferably comprises introducing the ligno-cellulosic feedstock in a soaking liquid comprising water at a temperature from 20° C. to 100° C., more preferably from 40° C. and 70° C. and for a soaking time which is from 30 seconds to 30 minutes, more preferably from 3 minutes to 15 minutes.

Optionally, the ligno-cellulosic feedstock is subjected to a preliminary hydrothermal treatment in water or a liquid comprising water to solubilize a portion of the water insoluble carbohydrates contained in the ligno-cellulosic feedstock prior to being introduced in the pressurized reactor vessel. The preliminary hydrothermal treatment is conducted in pressurized conditions in the presence of water in a steam or liquid phase, or mixture thereof, at a temperature from 100° C. to 190° C., preferably from 130° C. to 180° C., and most preferably from 140° C. to 170° C. The preliminary hydrothermal treatment is conducted for a time in a range from 10 minutes to 3 hours, preferably from 15 minutes to 3 hours, and most preferably from 20 minutes to 60 minutes. The preliminary hydrothermal treatment solubilizes mainly the hemicellulosic component of the ligno-cellulosic feedstock, which may subjected to thermal degradation at higher temperature, and a liquid comprising water and water soluble xylose polymers and oligomers and optionally other hemicellulose-derived sugars is thereby separated from the solid ligno-cellulosic feedstock.

The pre-treated ligno-cellulosic feedstock is subjected to enzymatic hydrolysis to hydrolyze the polymeric and oligomeric sugars to monomeric sugars, comprising glucose and xylose. Enzymatic hydrolysis comprises contacting the pre-treated ligno-cellulosic feedstock in slurry form with an enzyme or enzyme composition at conditions promoting the enzymatic activity. Thereby, a slurry of the pre-treated ligno-cellulosic feedstock is provided by mixing the pre-treated ligno-cellulosic feedstock with a liquid comprising water to have a dry matter content preferably between 10% and 25%; optionally, when the preliminary hydrothermal treatment is practiced, at least a portion of the liquid comprising water and solubilized xylose polymers and oligomers therein produced may also be used. Enzymatic hydrolysis is typically conducted at a pH between 4.5 and 5.0 at a temperature between 45° C. and 55° C., and for an hydrolysis time from 24 hours to 72 hours, under mixing agitation.

The enzymatic hydrolysis may be conducted in one or more steps. Preferably, the enzymatic hydrolysis is conducted in two steps in separated hydrolysis vessels. In the first hydrolysis steps, which is conducted for a time between 12 hours and 30 hours in a first vessel, a partial hydrolysis of the pre-treated ligno-cellulosic feedstock is obtained to obtain the liquefaction of the pre-treated ligno-cellulosic feedstock, thereby obtaining a partially hydrolyzed mixture having a viscosity lower that the initial slurry. The partially hydrolyzed mixture is then moved in a second hydrolysis vessel, wherein a second hydrolysis step is continued for a the time between 12 hours and 60 hours to obtain the ligno-cellulosic feedstock hydrolyzate slurry, comprising water, residual water insoluble pretreated ligno-cellulosic feedstock and water soluble glucose and xylose comprising glucose and xylose. The ligno-cellulosic feedstock hydrolyzate slurry may further comprise other C6 and C5 water soluble monomeric sugars, typically at concentration lower than glucose and xylose, respectively.

Even more preferably, enzymatic hydrolysis is conducted according the teaching of WO2010113130, which is herein incorporated by reference.

A portion of the residual water insoluble pretreated ligno-cellulosic feedstock may be removed from the ligno-cellulosic feedstock hydrolyzate slurry. Separation of residual water insoluble pretreated ligno-cellulosic feedstock may be obtained for instance by decanting, centrifuging, or pressing the ligno-cellulosic feedstock hydrolyzate slurry, or a combination thereof. Nevertheless, even if the presence of residual water insoluble pretreated ligno-cellulosic feedstock in the disclosed propagation process may give rise to mixing issues, some of the water soluble monomeric sugars soaked in the residual solids may be lost in the separation step, thereby in a preferred embodiment no solid removal is practiced.

The above described process or processes to derive the ligno-cellulosic feedstock hydrolyzate slurry from the ligno-cellulosic feedstock are exemplary and preferred embodiments to provide the ligno-cellulosic feedstock hydrolyzate slurry used as the main carbon source for producing a fermentation product according to the disclosed process, and it is understood that they are not intended to limit in any way the scope of the invention.

The ligno-cellulosic feedstock hydrolyzate slurry may have a dry matter content between 5% and 30%, preferably between 10% and 20%.

The ligno-cellulosic feedstock hydrolyzate slurry has a glucose concentration which may be from 20 g/Kg to 100 g/Kg of the ligno-cellulosic feedstock hydrolyzate slurry on a wet basis, preferably from 30 g/Kg to 70 g/Kg, and most preferably from 40 g/Kg to 50 g/Kg.

The ligno-cellulosic feedstock hydrolyzate slurry has a xylose concentration which may be from 10 g/Kg to 40 g/Kg of the ligno-cellulosic feedstock hydrolyzate slurry on a wet basis, preferably from 15 g/Kg to 30 g/Kg, and most preferably from 20 g/Kg to 25 g/Kg.

The ligno-cellulosic feedstock hydrolyzate slurry may further comprise inhibitors compounds selected from the lists of acetic acid, formic acid, furfural and hydroxymethyl furfural (5-HMF), which are formed in previous pretreatment and hydrolysis steps or processes, and inhibit the yeast growth, causing at least a delay in the growth rate.

Particularly, acetic acid may have a concentration which is in the range from 2 g/Kg to 7 g/Kg of the ligno-cellulosic feedstock hydrolyzate slurry on a wet basis.

The ligno-cellulosic feedstock hydrolyzate slurry may further contain biological contaminants, as typically occurs in operating at industrial scale. Biological contaminants are microbial organisms different from the yeast that is to be propagated according to the disclosed process, and whose presence is in general detrimental for the yield of the disclosed process, consuming a portion of the monomeric sugars totally available to the growth of the desired yeast. Biological contaminants may comprise bacteria and fungi, as well as yeasts different from the desired yeast to be propagated, such as wild-type yeasts. Bacteria Lactic acid bacteria, in particular *Lactobacillus* species, are the primary bacterial contaminants. Lactic acid concentrations of fermentation mixtures is usually taken as a measure of degree of contamination. Biological contamination has been controlled by means of sterilization of the ligno-cellulosic feedstock hydrolyzate, conversion media, and equipments involved in the process, which may be obtained by adding anti-bacterial agents, such as antibiotics or other aseptic agents, or by sterilization procedures, such as pasteurization, by applying physical agents, including among others, heat, light and radiation, before, between or during the course of fermentation/propagation runs. By "sterilization" is herein considered the reduction of the density of biological contaminants by a factor of at least 100. The use of anti-bacterial agents and sterilization procedures, which introduces additional costs, is preferably avoided in the disclosed process, at the same time keeping the growth of biological contaminants at a reasonable low level.

Preferably, the ligno-cellulosic feedstock hydrolyzate is not subjected to any sterilization step or procedure, which would be difficult and expensive to practice on industrial scale.

Preferably, no anti-bacterial agents are used in the disclosed process, neither are they added to the ligno-cellulosic feedstock hydrolyzate prior to the disclosed process.

The disclosed process comprises at least two conversion steps, which may be conducted in a unique vessel or in two separate vessels. In order to minimize the costs, the vessel or vessels are preferably not subjected to any sterilization and/or cleaning between and/or during conversion steps. Preferably, each conversion step is conducted in batch mode, wherein the ligno-cellulosic feedstock hydrolyzate slurry is added before starting the conversion step, or at the beginning of the conversion step.

A first conversion medium comprising a first portion of the ligno-cellulosic feedstock hydrolyzate and a starting amount of yeast is first created. To limit the effect of competitive growth of biological contaminants, in a preferred embodiment the ligno-cellulosic feedstock hydrolyzate slurry is maintained at a temperature from 45° C. to 55° C. prior to be used in the disclosed process, and most preferably at the temperature of the enzymatic hydrolysis or the final enzymatic hydrolysis step. At this temperature, the activity of the biological contaminants is significantly reduced. The temperature of the portion of the ligno-cellulosic feedstock hydrolyzate slurry used in the first conversion step is reduced to the temperature of the first conversion step, which is preferably in the range of 28° C. to 35° C. Heat exchangers may be used to cool down the first portion of the ligno-cellulosic feedstock hydrolyzate slurry to the temperature of the first conversion step in the first conversion vessel or before entering the first conversion vessel.

Water or a liquid comprising water, and optional limited amounts of additional carbon sources different from the ligno-cellulosic feedstock hydrolyzate slurry may be used to reach the desired dry matter content. One of the advantages offered by the disclosed process is the possibility of being conducted at a dry matter which is higher than other known processes which uses a ligno-cellulosic hydrolyzate slurry as the main carbon source. The dry matter content by weight of the first conversion medium is preferably less than 30%, as it would be difficult to be agitated, and it is preferably greater than 5%, more preferably greater than 10%, even more preferably greater than 15%, most preferably greater that 20%. Water or the liquid comprising water may be added at a temperature which is less than the first conversion temperature to cool down the first portion of the ligno-cellulosic feedstock hydrolyzate slurry.

Therefore, the density of biological contaminants in the first conversion medium at the begin of the first conversion step may be kept at a reasonable level, which may be in a range $10^0$ CFU/ml to $10^6$ CFU/ml, preferably from $10^1$ CFU/ml to $10^5$ CFU/ml, and most preferably from $10^1$ CFU/ml to $10^5$ CFU/ml of the first conversion medium.

The first conversion medium may further comprise a nitrogen source, typically urea, which is an inexpensive nutrient source for the yeast, but it is preferably free of added vitamins and/or trace elements, which are typically used on a laboratory scale as growth supplements but are extremely expensive. Stated in other words, preferably no vitamins and/or trace elements are added to the ligno-cellulosic feedstock hydrolyzate slurry and to the conversion media during the process or in steps prior to the process.

Preferably, the pH of the first conversion medium is adjusted to a value from 5.0 to 5.5, for instance by adding for instance a suitable amount of a base (NaOH solution). If needed to maintain the pH in the desired range, additional aliquots of the base may be added during first conversion step.

The yeast may be added to the first conversion medium, or to components used to form the first conversion medium. In one embodiment, the yeast is added to the first portion of the ligno-cellulosic feedstock hydrolyzate slurry used to form the first conversion medium. The amount of yeast contacted with the first conversion medium will vary according to the total volume of the first conversion medium. The yeast may be a fresh yeast or it may be a yeast produced in a previous propagation or conversion step. Preferably, in the first conversion step it is added an amount of yeast to have a starting yeast density which is between 1×10⁶ and 1×10⁸ yeast cells per milligram of the first conversion medium on a wet basis.

In the first conversion step, the yeast is maintained under conditions promoting the conversion of the water soluble glucose and xylose of the first conversion medium to a first propagated yeast and a first portion of the fermentation product, wherein a certain percent amount of the totally converted water soluble glucose and xylose is devoted to growth of yeast biomass. Thereby, the first conversion step is characterized by a first sugar-to-cells conversion ratio, which is the percent weight ratio by weight of water soluble glucose and water soluble xylose converted to the first propagated yeast to the total amount of water soluble glucose and xylose totally converted in the first conversion medium, on a carbon basis and since it is a percent weight ratio it is expressed as a percent. The first sugar-to-cells conversion ratio is in a range from 5% to 25%, preferably from 5% to 20%, and most preferably from 10% to 20%.

To calculate the sugar-to-cells conversion ratio of a conversion step, the amount of the totally converted water soluble glucose and xylose may be calculated by subtracting the concentration of water soluble glucose and xylose present in the conversion medium at the end of the conversion step to the concentration of water soluble glucose and xylose present in the conversion medium at the begin of the conversion step. Sugar concentration may be determined by standard HPLC analysis. Clearly, if some component is added to or removed from the conversion medium during the conversion step, it must be taken into account in the density determination, as is well known in the analytical arts. For instance, water may be added at a certain time to dilute the conversion medium, or a pH correction is needed, or additional sugar is added. In a preferred embodiment, the ligno-cellulosic feedstock hydrolyzate slurry further comprises residual enzymes from the hydrolysis step or steps, a portion of which are still active. Even if conversion conditions are not optimal for enzyme activity, a portion of the water insoluble carbohydrates in the residual water insoluble pre-treated ligno-cellulosic feedstock may be hydrolyzed to additional water soluble glucose and xylose which are therefore available to the yeast. Also in this case, the total amount of glucose and xylose converted by the yeast will take into account the additional water soluble glucose and xylose, which may be calculated from the measurement of the amount of water insoluble sugars in the residual water insoluble pretreated ligno-cellulosic feedstock at the end and at the begin of the conversion step. The totally converted water soluble glucose and xylose takes into account also the sugar uptake by biological contaminants.

Yeast cell density in terms of number of yeast cells per unit volume may be determined by cell count, or alternatively by means of optical transmittance measurement. Once the yeast density is known, yeast cell mean weight may be easily calculated by measuring the weight of yeast cells in a reference sample having a reference yeast density.

The sugar-to-cells conversion ratio of a conversion step is expressed on a carbon basis, that is as the ratio between the carbon contained in the yeast biomass on a dry basis at the end of the conversion step to the carbon contained in the totally converted water soluble glucose and xylose on a dry basis.

The carbon contained in the totally converted water soluble glucose and xylose may be derived by the carbon content in the water soluble glucose and xylose present in the conversion medium at the end and at the begin of the conversion step, as measured by standard elemental analysis. Alternatively, it may derived from the concentration of water soluble glucose and xylose converted by the yeast which are present in the conversion medium at the end and at the begin of the conversion step, considering the stoichiometric formulas of the water soluble glucose and xylose.

The carbon content in the yeast may be measured by standard elemental analysis of the dry yeast. Alternatively, it is may considered the reference sugar-to-cell ratio conversion which is commonly used in the art (see for instance The Alcohol Textbook, Fifth Edition, W. M. Ingledew et al., Nottingham University Press, Ethanol Technology Institute, 2009, p. 133), which is 0.50 g of yeast on a dry basis per gram of sugar. Thereby, if 2 gr of glucose are converted only to yeast, 1 gr of yeast on a dry basis is produced. For instance, if 1 gr of yeast is produced and 10 gr of glucose are totally converted, the sugar-to-cells conversion ratio is:

$$\text{sugar-to-cells conversion ratio} = (1 \text{ gr of yeast} \times 2 \text{ gr of glucose per gram of yeast})/10 \text{ gr of glucose} = 20\%.$$

The same reference conversion ratio of is 0.50 g of yeast on a dry basis per gram of sugar is valid also in the case of xylose. Thereby, it is sufficient to measure the weight of yeast produced, on a dry basis, and the amount of total sugars, including glucose and xylose, to easily calculate the sugar-to-cells conversion ratio of each conversion step.

As known in the art, aerobic conditions enhance the amount of propagated yeast produced. Aerobic conditions are characterized by a mean oxygen saturation in the conversion medium which is greater than 10%. Oxygen saturation is the ratio of the concentration of dissolved oxygen ($O_2$) in the conversion medium to the maximum amount of oxygen that will dissolve in the conversion medium at that temperature and pressure under stable equilibrium. Thereby, a flow of oxygen, air or other gas mixture comprising oxygen at a flow rate of 1 vvm or higher is typically inserted in the conversion medium. To promote the oxygen diffusion in the conversion medium, agitation or mixing of the conversion medium is also typically provided, which is difficult or expensive at high dry matter, due to high viscosity of the conversion medium.

In the disclosed process, the first sugar-to-cells conversion ratio at the end of the first conversion step is preferably obtained by maintaining aerobic conditions only for a portion of the first conversion step. Stated in other words, relative to the mean oxygen saturation in the conversion medium, the first conversion step comprises at least two phases, a first phase which is an aerobic phase, followed by an second phase which is an anaerobic phase. In a preferred embodiment, the aerobic phase is at the begin of the first conversion step, and it is reached by inserting air at a moderate flow rate which is in a range from 0.1 vvh to 10 vvh, preferably from 0.1 vvh to 5 vvh, and most preferably from 0.5 vvh to 3 vvh. The first portion of the ligno-cellulosic feedstock hydrolyzate slurry is introduced in the first conversion vessel by gravity from an inlet located at a height sufficient to create bubbling in the ligno-cellulosic feedstock hydrolyzate slurry or conversion medium already present in the first conversion vessel. The first portion of the ligno-cellulosic feedstock hydrolyzate slurry may be introduced so as to form a cascade to take advantage from the natural oxygenation of the ligno-cellulosic feedstock hydrolyzate slurry occurring during the transfer in the first conversion vessel. The initial level of oxygen saturation is at a high value, being preferably greater than 40%, and most preferably greater than 80%, and decreases during the first conversion step, due to the moderate air flow rate. The moderate air flow rate is used to slow down the natural decrease of the initial level of oxygen saturation, in order to obtain an aerobic phase which is preferably from 3 hours to 12 hours, more preferably from 5 hours to 10 hours, and most preferably from 7 hours to 8 hours. During the first conversion step, the first conversion medium is maintained under moderate agitation for at least a portion of the first conversion time in order to improve oxygen diffusion. Agitation may be reached by means of mechanical mixing means. Mixing is provided to slow down and homogenize the natural decrease of the initial level of oxygen saturation, and a moderate power is sufficient to obtain aerobic conditions for a time in the desired ranges, even in the case of a high dry matter slurry. The power used to agitate the first conversion medium may be measured in terms of the electric power used to agitate a ton of the first conversion medium on a wet basis, which is a weight power density, and a mean weight power density of less than 100 W/ton of the first conversion medium on a wet basis is preferably used in the disclosed process.

Glucose and xylose uptake rates is an important parameter of the disclosed process, especially in the case that ligno-cellulosic feedstock hydrolyzate comprises some biological contaminants and no sterilization and anti-bacterial agents are used, as in these conditions competitive growth of biological contaminants is enhanced. Glucose uptake by the yeast is favorite with respect to xylose uptake, thereby glucose concentration in the conversion medium will start decreasing, while xylose uptake will not proceed significantly until the glucose concentration is decreased below a certain critical value. As the affinity of the yeast to the remaining sugars (glucose and xylose) in the conversion medium decreases, the total uptake rate of glucose and xylose combined by the yeast will decrease over time, rendering the competitive growth of biological contaminants favorable. Thereby, in the disclosed process, the first conversion step is prolonged for a time sufficient to consume at least 50% of the glucose contained in the starting conversion medium, and less than 20% of the xylose contained in the starting conversion medium. It is intended that the glucose and xylose consumption is the total consumption occurred during the conversion step, and it can be verified by measuring the corresponding sugar concentration in the conversion medium. Thereby, the total combined glucose and xylose consumption occurring in the first conversion step includes also the combined glucose and xylose uptake by biological contaminants, which is intended to be minimized in the disclosed process, and the sugar eventually converted to the fermentation product. For improving the yield of the process in terms of yeast biomass produced, preferably the first conversion step is conducted for a first conversion time sufficient to consume at least 70% of the glucose of the starting conversion medium, and most preferably at least 80%. At the same time, for avoiding that the total sugar uptake rate reaches a critical value for competitive growth of biological contaminants, preferably the first conversion step is prolonged for a first conversion time sufficient to consume less than 10% of the xylose in the starting conversion medium, most preferably less than 5%. It is also noted that, while the total amount of xylose consumed in the first conversion step is preferably greater than 0, in some cases xylose may not be appreciably consumed at least in the first conversion step. The first conversion step may be conducted for a first conversion time which less than 30 hours, but preferably less than 20 hours, more preferably less than 15 hours, and most preferably less than 10 hours.

At the end of the first conversion step, a first conversion broth is obtained comprising water, a first propagated yeast and a first portion of the fermentation product. The amount of first propagated yeast which may be from 5 to 15 times the corresponding starting amount of yeast, as a result of the aerobic conditions imposed during a portion of the first conversion time. The same preferred range applies to the yeast cell density. Preferably, in the first conversion step the final yeast density is between $1 \times 10^7$ and $1 \times 10^9$ yeast cells per milligram of the first conversion medium on a wet basis. The first conversion broth further comprises water soluble glucose and xylose not consumed by the yeast and residual water insoluble pretreated ligno-cellulosic feedstock.

The first propagated yeast is then used in a second conversion step to convert a second portion of the ligno-cellulosic feedstock hydrolyzate slurry. In comparison with the first conversion step, the second conversion step is focused on the production of the fermentation product, but at the same time converting a small amount of water soluble glucose and xylose to a second yeast biomass. On the contrary to the first conversion step, the second conversion step converts the majority of the water soluble glucose and xylose available, and possibly all the water soluble glucose and xylose, thereby a second conversion time longer than the first conversion time is needed. The second conversion step is conducted to reach a higher sugar conversion yield than the first conversion step and the second yeast biomass is therefore produced in order to keep the second conversion time as low as possible, limiting the growth of biological contaminants. The second conversion step is conducted to have a second sugar-to-cells conversion ratio which is less than the first sugar-to-cells conversion ratio. The second sugar-to-cells conversion ratio is preferably greater than 2%. Even if some limited amount of yeast external to the disclosed process may be added in the second conversion step, it is preferred that only the first propagated yeast, or at least a portion thereof, is used. The second conversion time is greater than the first conversion time and preferably less than 72 hours, more preferably less than 60 hours, and most preferably less than 50 hours. In any case, it is desirable that at least 80% of the water soluble glucose and xylose totally available in the second conversion medium are converted in the second conversion step.

A second conversion medium is created from at least a portion of the first propagated yeast and a second portion of the ligno-cellulosic feedstock hydrolyzate slurry. The procedure used to form the second conversion medium is similar to the procedure to form the first conversion medium, and the same preferred embodiments apply mutatis mutandis to the creation of the second conversion medium. In a preferred embodiment, the first propagated yeast is not separated from the first conversion broth before being used to create the second conversion medium, and at least a portion of the first populated broth and the second portion of the ligno-cellulosic feedstock hydrolyzate slurry are mixed together in a second conversion vessel to form the second conversion medium. The remnant water soluble glucose and xylose which have been not converted in the first conversion step are therefore available to be converted in the second conversion step and are not wasted. In this embodiment, the second conversion medium at the begin of the second conversion step will further comprise the first portion of the fermentation product produced in the first conversion step. Preferably, the amount of the first conversion broth and the second portion of the ligno-cellulosic feedstock hydrolyzate slurry are selected to have a starting yeast density in the second conversion step which is greater than the starting yeast density in the first conversion step. A high starting yeast density is preferred to reduce the second conversion time. The starting yeast density in the second conversion step may be between $1 \times 10^6$ and $1 \times 10^8$ yeast cells per milligram of the second conversion medium on a wet basis. The first conversion broth and the second portion of the ligno-cellulosic feedstock hydrolyzate slurry are preferably in a weight ratio on a wet basis which is from 1:2 to 1:10, and most preferably from 1:3 to 1:8.

As in the first conversion step, also in the second conversion step the second portion of the ligno-cellulosic feedstock hydrolyzate slurry is preferably maintained at a temperature from 45° C. to 55° C. prior to be used to create the second conversion medium, to limit the effect of competitive growth of biological contaminants.

Therefore, the density of biological contaminants in the second conversion medium at the begin of the second conversion step may be kept at a reasonable level, which may be in a range $10^0$ CFU/ml to $10^6$ CFU/ml, preferably from $10^1$ CFU/ml to $10^5$ CFU/ml, and most preferably from $10^2$ CFU/ml to $10^3$ CFU/ml of the second conversion medium.

In order to keep the second sugar-to-cells conversion ratio low, the second conversion step is conducted in anaerobic conditions, or prevalently in anaerobic conditions, that is anaerobic conditions are maintained for at least 80% of the second conversion time. If present, an aerobic phase may be present preferably at the beginning of the second conversion step. Namely, similarly to the first conversion step, the second portion of the ligno-cellulosic feedstock hydrolyzate slurry and/or the first populated broth are preferably introduced in the first conversion vessel by gravity from an inlet located at a height sufficient to create bubbling in the ligno-cellulosic feedstock hydrolyzate slurry and/or conversion medium already present in the second conversion vessel. The ligno-cellulosic feedstock hydrolyzate slurry may be introduced so as to form a cascade to take advantage from the natural oxygenation of the ligno-cellulosic feedstock hydrolyzate slurry occurring during the transfer in the second conversion vessel. Preferably, air is not introduced in the second conversion step.

During the second conversion step, the second conversion medium may be maintained under moderate agitation for at least a portion of the second conversion time in order to improve homogeneity of the slurry. Agitation may be reached by means of mechanical mixing means. Mixing is provided to slow down and homogenize the natural decrease of the initial level of oxygen saturation. The power used to agitate the second conversion medium. A mean weight power density of less than 100 W/ton of the second conversion medium on a wet basis is preferably used.

The second conversion step produces a second fermentation broth in a slurry form, comprising water, the fermentation product and residual water insoluble pretreated ligno-cellulosic feedstock. The fermentation product which can be separated and recovered from the second fermentation broth.

EXPERIMENTAL

Preparation of the Ligno-Cellulosic Feedstock Hydrolysate

Wheat straw was selected for proving the disclosed process.

First, the feedstock was subjected to a pretreatment process, by applying a preliminary hydrothermal treatment at a temperature of 158° C. for 65 minutes, with a first solubilization of the raw material. The process generated a pre-treated feedstock slurry, that was separated in a liquid portion, comprising mainly xylooligomers, and a solid portion by means of a press. The solid portion was subjected to a hydrothermal treatment with steam at 204° C. for 4 minutes, followed by steam explosion, to generate a solid pre-treated ligno-cellulosic feedstock.

The solid pre-treated ligno-cellulosic feedstock and the liquid portion comprising xylooligomers were mixed in a bioreactor, and water was added to obtain a pre-treated ligno-cellulosic feedstock slurry having a dry matter content of 15% by weight, pH was adjusted to 5.0±0.2 by NaOH addition, then the pre-treated ligno-cellulosic feedstock slurry subjected to enzymatic hydrolysis.

A commercial enzymatic cocktail CTec3 by Novozymes, capable of hydrolyzing both C6 and C5 sugars, was added corresponding to a dosage of 7% protein mg per grams of glucans in the pre-treated ligno-cellulosic feedstock and the slurry was hydrolyzed at 50° C. under continuous stirring for 72 hours.

The resulting ligno-cellulosic feedstock hydrolysate was a slurry, having a dry matter of 15% by weight, comprising a liquid fraction and a residual water insoluble pretreated ligno-cellulosic feedstock.

The ligno-cellulosic feedstock hydrolysate slurry was maintained at the temperature of 50° C. until its use in the following propagation experiments. No antibiotics was introduced.

CONVERSION EXPERIMENTS

The disclosed process was proven both on lab scale and industrial scale. Experiments were performed without any sterilization between the conversion steps, and between experiments.

Lab Scale

First Lab Experiment

In the first conversion step, the first conversion medium was formed inserting a volume of 1.21 of hot ligno-cellulosic feedstock hydrolysate slurry in a first bioreactor and supplementing with urea solution at 1.5 g/l. pH was set at 5.2±0.1 by NaOH control. No vitamins and other nutrients were used. The conversion medium was cooled to 32° C. before inserting the yeast. Dry matter was about 15%. The composition on a wet basis of the first conversion medium, corresponding approximately to the composition of the ligno-cellulosic feedstock hydrolysate slurry, is reported in table 1. The compositions are given in terms of the water soluble components which are relevant for the process and the residual water insoluble pretreated ligno-cellulosic feedstock is separated in its main components (insoluble glucans, insoluble xylans and Lignin and other insolubles). Acetic acid, formic acid, furfural, hydroxymethyl furfural are inhibitory compounds of yeast propagation.

Lactic acid is produced by bacterial contamination and therefore is considered as a marker of bacterial presence. Thereby, a certain biological contamination was present in the ligno-cellulosic feedstock hydrolysate.

First conversion step was conducted under agitation by mixing the cultivation medium with an impeller at 300 rpm in batch configuration, inserting an air flow of 1 VVh. VVh corresponds to the gas volume that is flowing per conversion medium volume per hour.

Yeast cell density was determined by cell count (Neubauer cell counting chamber) and the composition of the first conversion medium was analyzed by HPLC to determine concentration for residual glucose and xylose and critical compounds for yeast propagation. Both the measurements were performed at the begin and at the end of the conversion step.

A commercial genetically modified yeast CelluX™2 distributed by Leaf Technologies, capable to ferment glucose and xylose, was inserted in the first conversion medium at a starting yeast density of $1.3 \times 10^7$ yeast cells per milligram of the first conversion medium, corresponding to 0.2 g of yeast on a dry basis per gram of the first conversion medium.

First conversion step was conducted for a first conversion time of 14 hours for taking into account the initial lag phase needed to let the yeast to adapt to the conversion medium. Oxygen saturation, $pO_2$, was measured during the conversion step by means of a $pO_2$ probe Mettler Toledo InProbe 6820 inserted in the conversion medium after calibration and it is reported in FIG. 1. $pO_2$ remained at an almost stable level close to about 70% for about 3 hours, indicating that the yeast was almost inactive as expected during the lag phase, then progressively decreases to 10% in about 6.5 hours.

A yeast cell concentration of $1.5 \times 10^8$ yeast cells per milligrams was achieved in the first conversion broth. Growth performances were evaluated by calculating a growth factor, that is the ratio between yeast cell concentration at the end and at the start of the conversion. A growth factor of about 11.5 was obtained in the first conversion step, corresponding to about 2 g of yeast on a dry basis per Kg of the first conversion medium.

The composition of the first conversion broth is reported in table 1. Despite the presence of remnant enzymes from previous hydrolysis step, the high sugar concentration in the conversion broth inhibited further hydrolysis of the oligomeric sugars and the insoluble glucans and xylans.

About 33.9 g/Kg of glucose were converted (corresponding to about 76% of the initial glucose) and about 1.3 g/Kg of xylose (corresponding to about 7% of the initial xylose) were consumed in the first conversion step. Considering the a reference conversion ratio of 0.50 g of yeast per gram of sugar, about 4.2 gr of sugars of first conversion medium were thereby converted to yeast, per Kg of cultivation medium, with a sugar-to-cell conversion ratio of about 11%.

The concentration of lactic acid did not increase significantly, indicating that propagation of bacterial contaminants was at reasonable levels. A certain amount of ethanol was also produced.

TABLE 1

Composition of the starting conversion media (t = 0 h) and the conversion broths (t = 14 h, t = 6 h) of the experiments on a lab scale.

| | | Concentration [g/Kg] | | | | | | | |
|---|---|---|---|---|---|---|---|---|---|
| | | First lab scale experiment | | | | Second lab scale experiment | | | |
| | | First conversion step | | Second conversion step | | First conversion step | | Second conversion step | |
| | | t = 0 h | t = 14 h | t = 0 h | t = 48 h | t = 0 h | t = 6 h | t = 0 h | t = 48 h |
| Water soluble components | glucose | 44.49 | 10.6 | 34.64 | 0.01 | 38.08 | 12.77 | 33.98 | 0.11 |
| | xylose | 17.86 | 16.57 | 16.54 | 0.8 | 18.09 | 17.07 | 15.97 | 0.73 |
| | glycerol | 0.29 | 1.79 | 0.63 | 1.95 | 0.71 | 1.54 | 0.44 | 1.96 |
| | formic acid | 0.71 | 0.85 | 0.87 | 0.55 | 0.93 | 0.7 | 0.8 | 0.9 |
| | lactic acid | 0.19 | 0.22 | 0.24 | 0.27 | 0.2 | 0.24 | 0.26 | 0.26 |
| | acetic acid | 2.49 | 2.18 | 2.24 | 1.82 | 2.44 | 2.14 | 2.24 | 1.85 |
| | ethanol | 0 | 16.75 | 3.35 | 27.09 | 3.78 | 15.46 | 3.09 | 27.18 |
| | 5-HMF | 0.06 | 0.01 | 0.04 | 0 | 0.04 | 0.02 | 0.04 | 0 |
| | furfural | 0.05 | 0 | 0.04 | 0 | 0.02 | 0 | 0.03 | 0 |
| | Glucose oligomers | 7.44 | 5.38 | 7.38 | 5.21 | 7.03 | 6.82 | 7.32 | 5.80 |
| | Xylose oligomers | 5.68 | 4.82 | 5.72 | 5.33 | 5.51 | 5.23 | 5.59 | 4.90 |
| Water insoluble components | Insoluble glucans | 18.62 | 18.60 | 18.63 | 15.51 | 18.62 | 18.65 | 18.63 | 16.89 |
| | Insoluble xylans | 2.46 | 2.46 | 2.46 | 2.45 | 2.46 | 2.45 | 2.46 | 2.24 |
| | Lignin and other insolubles | 49.8 | 50.4 | 49.8 | 50.1 | 49.9 | 50.0 | 49.8 | 50.1 |

In the second conversion step, an aliquot of 960 ml of hot ligno-cellulosic feedstock hydrolysate was introduced in a second bioreactor, identical to the first bioreactor, cooled to about 32° C., then a volume of 240 ml of the first conversion broth was added to form the second conversion medium. pH was set at 5±0.1 by NaOH solution and supplemented with urea solution at 1.0 g/l. Thereby, in the second conversion step, the volume of the first conversion broth was about 1:5 the total volume of the second conversion medium. The composition of the second conversion medium is reported in Table 1. It is noted that the second conversion medium contains some ethanol from the first conversion broth diluted with fresh ligno-cellulosic feedstock hydrolysate slurry; ethanol concentration was sufficiently low to not create problems to the second conversion step. Starting glucose and xylose concentration were lower than in the first conversion step, as some sugars were consumed.

The starting yeast density was of about $3.2 \times 10^7$ yeast cells per milligram of the second conversion medium, corresponding to about 0.5 g of yeast on a dry basis per gram of the second conversion medium. PO2 concentration of the second conversion step, reported in FIG. 1, decreased from 50% to 10% in about 2 hours.

The second conversion was performed for 48 hours in absence of air flow, in batch configuration, maintaining a temperature of 32° C. under agitation at 300 rpm. In the second conversion step, enzymatic hydrolysis of the residual water insoluble pretreated ligno-cellulosic feedstock was continued by the enzymes contained in the ligno-cellulosic feedstock hydrolysate and some additional sugars were made available to the yeast.

A yeast cell concentration of $1.6 \times 10^8$ yeast cells per milligrams was achieved in the second conversion broth, thereby a growth factor of about 5 was obtained, corresponding to about 2.5 g of yeast on a dry basis per Kg of the second conversion medium.

The compositions of second conversion broth shows that almost all the monomeric sugars in the second conversion medium were consumed by the propagated yeast, as well as additional monomeric sugars hydrolyzed in the second conversion step, which maintained its capability of fermenting both glucose and xylose. About 55 gr of sugars/Kg of first conversion medium were thereby converted to yeast, with a sugar-to-cell conversion ratio of about 9%.

Bacterial contamination was very low or negligible, as evidenced by lactic acid concentration which was stable.

The efficiency of whole conversion process is typically described by means of the sugar-to-ethanol conversion factor on a carbon basis. As known in the art, the ideal sugar-to-ethanol conversion factor is 0.51. This corresponds to the maximum conversion of sugars to ethanol, without yeast propagation, as described by the stoichiometric formulations. The total sugar-to-ethanol conversion factor is about 0.43, showing that the disclosed process reaches a high ethanol yield with a very low amount of yeast external to the process.

Second Lab Experiment

The second experiment was conducted as in the first experiment, but the remnant aliquot of the first conversion broth in the first experiment was used as inoculum instead of fresh dry yeast. Moreover, first conversion step was conducted for 6 hours, as the yeast was already adapted to the conversion medium. Composition of the conversion medium and broths are reported in Table 1. The glucose content in the first conversion medium was slightly less than in the first experiment, as some glucose in the residual aliquot from the first experiment was converted. Moreover, some ethanol was present even if at a no problematic level. $pO_2$ of the first conversion step is reported in FIG. 1. $pO_2$ of the second conversion step was almost identical to the corresponding step of the first experiment.

Main parameters and result of first conversion step:
Starting yeast density: $5.3 \times 10^7$ yeast cells per milligram
Final yeast cell density: $1.7 \times 10^8$ yeast cells per milligrams
Growth factor: about 3.2
Weight of produced yeast: 1.8 g of yeast on a dry basis per Kg
Total sugar converted: 26 g/Kg
Sugar-to-cell conversion ratio: 13.4%.
Main parameters and result of second conversion step:
Starting yeast density: $3.4 \times 10^7$ yeast cells per milligram
Final yeast cell density: $1.5 \times 10^8$ yeast cells per milligrams
Growth factor: about 4.4
Weight of produced yeast: 1.8 g of yeast on a dry basis per Kg
Total sugar converted: 59 g/Kg
Sugar-to-cell conversion ratio: 8%.
Total sugar-to-ethanol conversion factor of the whole process: 0.43.

Industrial Scale Validation

The conversion process was tested on an industrial scale equipment. Procedure used was transposed from lab scale experiments.

The first conversion step was conducted in a first cylindrical vessel. The agitation was provided by an impeller coaxial to the vessel axis, rotated at 38 rpm.

The second conversion step was conducted in a second cylindrical vessel. The agitation was provided by an impeller coaxial to the vessel axis, rotated at 20 rpm.

pO2 was measured by means of a set of probes disposed in different positions inside the conversion medium.

$pO_2$ curves showed profiles similar to lab scale experiments.

The first conversion vessel was filled with 350 m³ of first cultivation medium and the first conversion step was conducted for 18 hours. The second conversion step was conducted for 60 hours on 1200 m³ of total second cultivation medium, which was formed according to the ratio 4:1 (fresh hydrolyzate:first converted broth).

Both lab scale experiments were scaled-up on industrial scale.

Main parameters and result of first conversion step:

|  | First lab scale exp conditions | Second lab scale exp conditions |
| --- | --- | --- |
| Glucose conversion: | 84% | 97% |
| Xylose conversion: | 15% | 13% |
| Sugar-to-cell conversion ratio: | 17% | 20% |
| Main parameters and result of second conversion step: | | |
| Sugar-to-cell conversion ratio: | 12% | 15% |

The mean electrical power consumption was about 90 W/ton of the first conversion medium on a wet basis over the whole process.

Different runs were conducted, with mean electrical power consumption of less than 100 W/ton of the first conversion medium. In some cases a mean electrical power consumption of less than 80 W/ton was attained.

The industrial scale validation shows that the disclosed process can reach a high ethanol yield with a minimum amount of yeast external to the process, low bacterial contamination and a very low power consumption.

The invention claimed is:

1. A process to produce a fermentation product from a ligno-cellulosic feedstock hydrolyzate slurry comprising water, water soluble glucose and water soluble xylose and water insoluble pretreated lignocellulosic feedstock, said process comprising the steps of:
    creating a first conversion medium comprising a first portion of the ligno-cellulosic feedstock hydrolyzate slurry and a yeast capable of converting glucose and xylose to a propagating yeast and a fermentation product;
    allowing the yeast to convert less than 20% of the water soluble xylose and at least 50% of the water soluble glucose of the first conversion medium to a first propagated yeast and a first portion of the fermentation product in a first conversion step having a first sugar-to-cells conversion ratio in a range of from 5% to 25%, wherein the first sugar-to-cells conversion ratio is a percent weight ratio of the glucose and xylose converted to the propagated yeast in the first conversion step to the water soluble glucose and xylose totally converted in the first conversion medium, on a carbon basis, wherein the first conversion step is conducted for a first conversion time, in which the conversion time is in the range of 10 to 30 hours with a starting yeast density between $1 \times 10^6$ and $1 \times 10^8$ yeast cells per milligram of the first conversion medium on a wet basis;

creating a second conversion medium comprising at least a portion of the first propagated yeast and a second portion of the ligno-cellulosic feedstock hydrolyzate slurry;

allowing the yeast to convert at least a portion of the water soluble glucose and xylose in the second conversion medium to at least a second propagated yeast and a second portion of the fermentation product in a second conversion step having a second sugar-to-cells conversion ratio which is less than the first sugar-to-cells conversion ratio, wherein the second sugar-to-cells conversion ratio is a percent weight ratio of the water soluble glucose and xylose converted to the propagated yeast in the second conversion step to totally converted water soluble glucose and xylose in the second conversion medium, on a carbon basis.

2. The process of claim 1, wherein the first conversion step comprises at least a first phase which is an aerobic phase and a second phase which is an anaerobic phase.

3. The process of claim 1, wherein the first conversion step is conducted by inserting air at a flow rate which is in a range selected from the group consisting of from 0.1 vvh to 10 vvh, from 0.1 vvh to 5 vvh, and from 0.5 vvh to 3 vvh.

4. The process of claim 1, wherein the first conversion step is conducted by mixing the first conversion medium at a weight power density of less than 100 W/ton of the first conversion medium on a wet basis.

5. The process of claim 1, wherein the second conversion step is conducted for a second conversion time is greater than the first conversion time and less than a value selected from the group consisting of 72 hours, 60 hours, and 50 hours.

6. The process of claim 1, wherein the second conversion step is conducted in anaerobic conditions for at least 80% of the second conversion time.

7. The process of claim 1, wherein the first conversion medium and the second conversion medium have a dry matter content which is less than 30% and greater than a percent value selected from the group consisting of 5%, 10%, 15%, and 20%.

8. The process of claim 1, wherein the first conversion medium and the second conversion medium further comprise a nitrogen source.

9. The process of claim 1, wherein the first conversion step and the second conversion step are conducted in separated vessels.

10. The process of claim 1, wherein the fermentation product is ethanol.

11. The process of claim 3, wherein the first sugar-to-cells conversion ratio is in a range selected from the group consisting of from 5% to 20%, and from 10% to 20%.

12. The process of claim 5, wherein the second sugar-to-cells conversion ratio is greater than 2%.

13. The process of claim 5, wherein at least 80% of the water soluble glucose and xylose are converted in the second conversion step.

14. The process of claim 8, wherein no vitamins and/or trace elements are added to the process.

15. The process of claim 8, wherein the ligno-cellulosic feedstock hydrolyzate slurry is not subjected to any sterilization.

16. The process of claim 1, wherein the first conversion step has a final yeast density which is between $1 \times 10^7$ and $1 \times 10^9$ yeast cells per milligram of the first conversion medium on a wet basis.

17. The process of claim 1, wherein the second conversion step has a starting yeast density which is greater than the starting yeast density in the first conversion step.

* * * * *